US011793557B2

(12) United States Patent
Tempco et al.

(10) Patent No.: US 11,793,557 B2
(45) Date of Patent: Oct. 24, 2023

(54) SYSTEM AND METHOD OF MANUFACTURE FOR SPINAL IMPLANT

(71) Applicant: WARSAW ORTHOPEDIC INC., Warsaw, IN (US)

(72) Inventors: Dale A. Tempco, Germantown, TN (US); Rodney Ray Ballard, Lakeland, TN (US); Matthew D. May, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 2 days.

(21) Appl. No.: 17/532,387

(22) Filed: Nov. 22, 2021

(65) Prior Publication Data

US 2022/0079644 A1 Mar. 17, 2022

Related U.S. Application Data

(62) Division of application No. 15/666,305, filed on Aug. 1, 2017, now Pat. No. 11,229,465.

(51) Int. Cl.
*B33Y 10/00* (2015.01)
*B29C 64/153* (2017.01)
(Continued)

(52) U.S. Cl.
CPC .......... *A61B 17/7098* (2013.01); *A61B 17/70* (2013.01); *A61B 17/84* (2013.01);
(Continued)

(58) Field of Classification Search
CPC . A61B 17/8625; A61B 17/8635; A61B 17/86; A61B 17/866; A61B 17/863;
(Continued)

(56) References Cited

U.S. PATENT DOCUMENTS

| 5,204,055 A | 4/1993 | Sachs et al. |
| 8,801,762 B2 | 8/2014 | Willert et al. |

(Continued)

FOREIGN PATENT DOCUMENTS

| CN | 204581484 U | 8/2015 |
| EP | 3135408 A1 | 10/2019 |
| WO | 2016082880 A1 | 6/2016 |

OTHER PUBLICATIONS

Wikipedia contributors. (Mar. 5, 2023). Electrical resistivity and conductivity. In Wikipedia, The Free Encyclopedia. Retrieved 19:50, Mar. 21, 2023, from https://en.wikipedia.org/w/index.php?title=Electrical_resistivity_and_conductivity&oldid=1143014793 (Year: 2023).*

(Continued)

*Primary Examiner* — Michael M. Robinson
(74) *Attorney, Agent, or Firm* — Sorell, Lenna & Schmidt, LLP

(57) ABSTRACT

A build plate includes a surface that defines at least one opening configured for disposal of a proximal portion of a screw shaft. The proximal portion is formed by a first manufacturing method and defines a distal face. The proximal portion is connected with the surface in a configuration to orient the distal face for forming a distal portion of the screw shaft thereon by a second manufacturing method that includes an additive manufacturing apparatus. In some embodiments, systems, spinal constructs, surgical instruments and methods are disclosed.

20 Claims, 11 Drawing Sheets

(51) Int. Cl.

| | | |
|---|---|---|
| *B29C 64/245* | (2017.01) | |
| *B29C 64/386* | (2017.01) | |
| *B29C 64/393* | (2017.01) | |
| *A61B 17/84* | (2006.01) | |
| *A61B 17/86* | (2006.01) | |
| *B22F 10/28* | (2021.01) | |
| *B22F 12/30* | (2021.01) | |
| *B22F 12/41* | (2021.01) | |
| *B22F 12/67* | (2021.01) | |
| *B22F 10/00* | (2021.01) | |
| *B22F 3/11* | (2006.01) | |
| *A61B 17/70* | (2006.01) | |
| *B33Y 30/00* | (2015.01) | |
| *B33Y 50/00* | (2015.01) | |
| *B33Y 50/02* | (2015.01) | |
| *B33Y 80/00* | (2015.01) | |
| *A61B 17/00* | (2006.01) | |
| *A61F 2/30* | (2006.01) | |
| *B22F 5/06* | (2006.01) | |
| *B22F 7/06* | (2006.01) | |
| *B22F 7/08* | (2006.01) | |
| *B29K 105/00* | (2006.01) | |
| *B22F 10/12* | (2021.01) | |
| *B22F 10/18* | (2021.01) | |
| *B22F 10/66* | (2021.01) | |

(52) U.S. Cl.
CPC ............ *A61B 17/86* (2013.01); *A61B 17/863* (2013.01); *A61B 17/866* (2013.01); *A61B 17/8625* (2013.01); *A61B 17/8635* (2013.01); *B22F 10/28* (2021.01); *B22F 12/30* (2021.01); *B22F 12/41* (2021.01); *B22F 12/67* (2021.01); *B29C 64/153* (2017.08); *B29C 64/245* (2017.08); *B29C 64/386* (2017.08); *B29C 64/393* (2017.08); *B33Y 10/00* (2014.12); *B33Y 30/00* (2014.12); *B33Y 50/00* (2014.12); *B33Y 50/02* (2014.12); *B33Y 80/00* (2014.12); *A61B 17/864* (2013.01); *A61B 17/8605* (2013.01); *A61B 2017/00004* (2013.01); *A61B 2017/00526* (2013.01); *A61B 2017/00889* (2013.01); *A61B 2017/00893* (2013.01); *A61B 2017/00964* (2013.01); *A61B 2017/8655* (2013.01); *A61F 2002/30962* (2013.01); *B22F 3/1103* (2013.01); *B22F 5/06* (2013.01); *B22F 7/06* (2013.01); *B22F 7/062* (2013.01); *B22F 7/08* (2013.01); *B22F 10/00* (2021.01); *B22F 10/12* (2021.01); *B22F 10/18* (2021.01); *B22F 10/66* (2021.01); *B22F 2207/17* (2013.01); *B22F 2998/10* (2013.01); *B22F 2999/00* (2013.01); *B29K 2105/251* (2013.01)

(58) Field of Classification Search
CPC ..... A61B 17/84; A61B 17/70; A61B 17/7098; A61B 2017/00004; A61B 17/864; A61B 2017/8655; A61B 2017/00964; A61B 2017/00893; A61B 2017/00889; A61B 17/8605; A61B 2017/00526; A61B 2017/561; B29C 64/393; B29C 64/245; B29C 64/386; B29C 64/153; B33Y 50/02; B33Y 30/00; B33Y 80/00; B33Y 50/00; B33Y 10/00; B22F 2998/10; B22F 5/06; B22F 7/062; B22F 7/06; B22F 3/1103; B22F 2999/00; B22F 7/08; B22F 2207/17; B22F 3/1055; B22F 5/00; B22F 2005/004; A61F 2002/30962; B29K 2105/251

See application file for complete search history.

(56) References Cited

U.S. PATENT DOCUMENTS

| | | |
|---|---|---|
| 2010/0094420 A1 | 4/2010 | Grohowski, Jr. |
| 2014/0159266 A1 | 6/2014 | Bamberg et al. |
| 2014/0252685 A1 | 9/2014 | Stucker et al. |
| 2015/0018956 A1 | 1/2015 | Steinmann et al. |
| 2015/0134063 A1 | 5/2015 | Stienmann et al. |
| 2015/0150557 A1 | 6/2015 | Tsai et al. |
| 2015/0313658 A1 | 11/2015 | Kolb |
| 2016/0157908 A1 | 6/2016 | Cawley et al. |
| 2016/0339519 A1* | 11/2016 | Sargent ................. B22F 10/36 |
| 2017/0056975 A1 | 3/2017 | Carter et al. |
| 2017/0135706 A1 | 5/2017 | Frey et al. |
| 2018/0141277 A1* | 5/2018 | Warner ................. B29C 64/30 |

OTHER PUBLICATIONS

European Patent Organisation (EPO), Erhardtstrasse 27, 80331, Munich, Germany—Supplementary Search Report, Application No. EP20180841253 dated Jul. 24, 2018, Date of dispatch: Mar. 26, 2021.
China National Intellectual Property Administration, Application/Patent No. 201880049964.1, Notice on the Third Office Action, Date of Dispatch: Oct. 28, 2022.

* cited by examiner

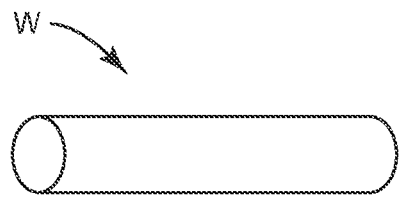
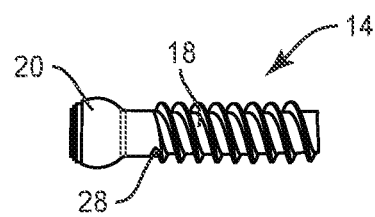
FIG. 4　　　　　　　　FIG. 5
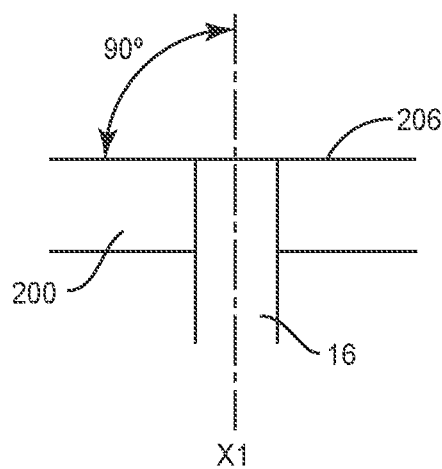
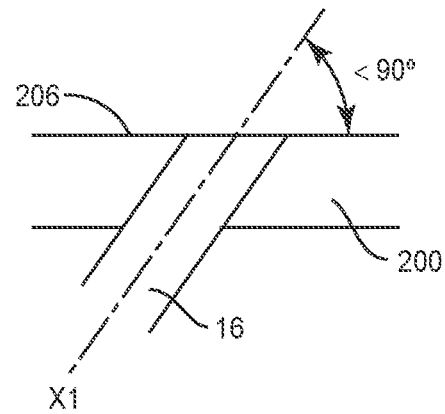
FIG. 6　　　　　　　　FIG. 7

SYSTEM AND METHOD OF MANUFACTURE FOR SPINAL IMPLANT

CROSS-REFERENCE TO RELATED APPLICATIONS

This application is a division of U.S. patent application Ser. No. 15/666,305, filed on Aug. 1, 2017, which is incorporated by reference herein, in its entirety.

TECHNICAL FIELD

The present disclosure generally relates to medical devices for the treatment of spinal disorders, and more particularly to a spinal implant system having spinal implants manufactured by a method including a plurality of manufacturing techniques.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including bone fasteners are often used to provide stability to a treated region. Such bone fasteners are traditionally manufactured using a medical machining technique. This disclosure describes an improvement over these prior technologies.

SUMMARY

In one embodiment, a build plate is provided. The build plate includes a surface that defines at least one opening configured for disposal of a proximal portion of a screw shaft. The proximal portion is formed by a first manufacturing method and defines a distal face. The proximal portion is connected with the surface in a configuration to orient the distal face for forming a distal portion of the screw shaft thereon by a second manufacturing method that includes an additive manufacturing apparatus. In some embodiments, systems, spinal constructs, spinal implants, surgical instruments and methods are disclosed.

In one embodiment, a method for fabricating a bone fastener is provided. The method comprises the steps of: disposing a build plate with a working chamber of an additive manufacturing apparatus, the plate including at least one selectively oriented opening configured for disposal of a proximal portion of a screw shaft, the proximal portion defining a distal face; connecting the proximal portion with the plate in a configuration to orient the distal face for forming a distal portion of the screw shaft thereon by the additive manufacturing apparatus based on selected configuration parameters; and forming the distal portion by heating a material in a layer by layer formation of the distal portion onto the distal face such that a processor instructs the additive manufacturing apparatus to form the distal portion onto the distal face.

In one embodiment, an additive manufacturing apparatus is provided. The additive manufacturing apparatus includes an enclosure that defines a working chamber and a laser device. A selectively configured build plate is disposed in the working chamber. The plate defines at least one opening configured for disposal of a proximal portion of a screw shaft. The proximal portion is formed by a medical machining method and defines a distal face. The proximal portion is connected with the plate in a configuration to orient the distal face for forming a distal portion of the screw shaft thereon by selective laser melting of a material onto the distal face to form the distal portion with a powder bed process.

BRIEF DESCRIPTION OF THE DRAWINGS

The present disclosure will become more readily apparent from the specific description accompanied by the following drawings, in which:

FIG. 4 is a side view of components of one embodiment of a system in accordance with the principles of the present disclosure;

FIG. 5 is a side view of components of one embodiment of a system in accordance with the principles of the present disclosure;

FIG. 6 is a side view of components of one embodiment of a system in accordance with the principles of the present disclosure;

FIG. 7 is a side view of components of one embodiment of a system in accordance with the principles of the present disclosure;

DETAILED DESCRIPTION

Figure 1:
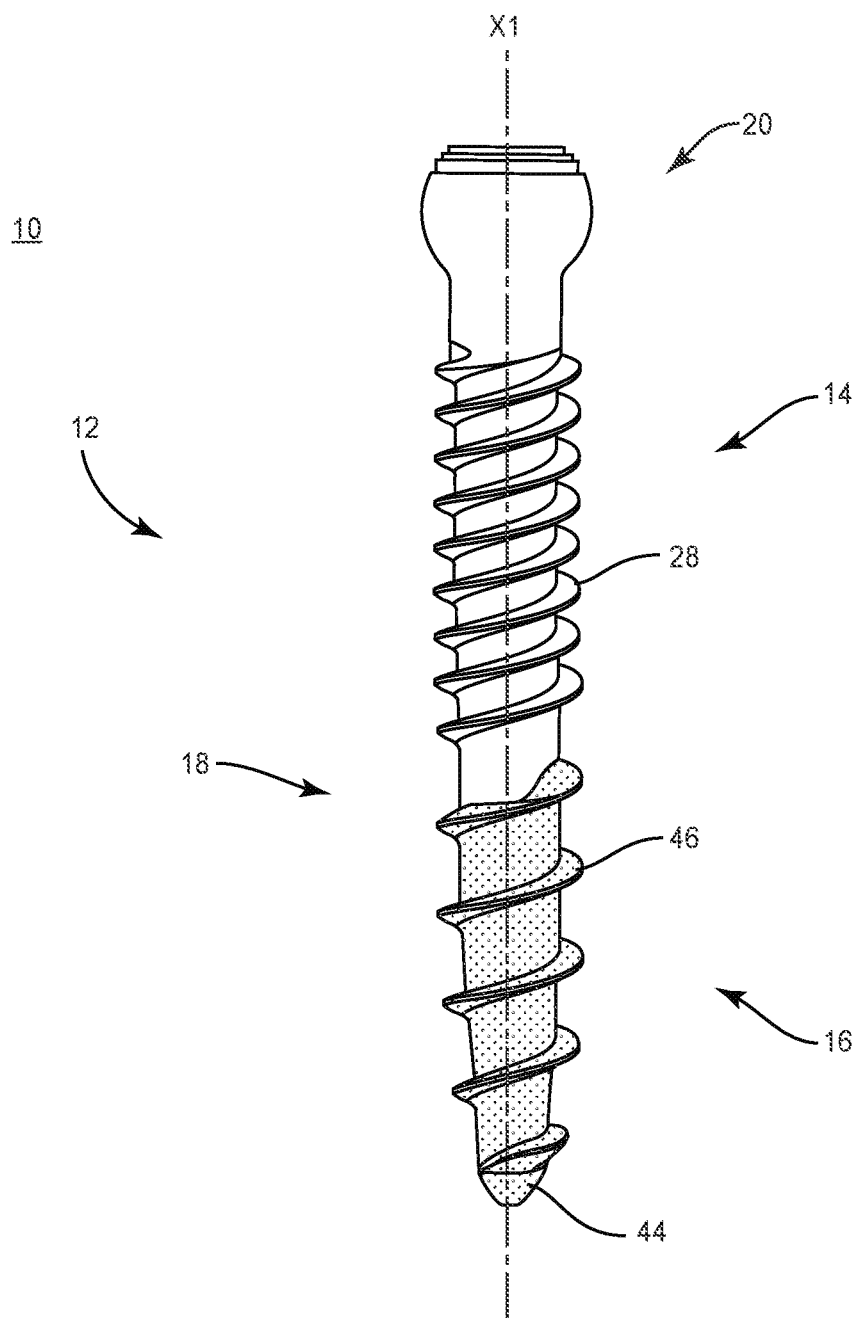
FIG. 1 is a side view of components of one embodiment of a system in accordance with the principles of the present disclosure.

The exemplary embodiments of a surgical system and related methods of use disclosed are discussed in terms of medical devices for the treatment of musculoskeletal disorders and more particularly, in terms of a spinal implant system having spinal implants manufactured by a method including a plurality of manufacturing techniques. In some embodiments, the spinal implant system includes a spinal implant comprising a bone screw including a hybrid medical device. In some embodiments, the spinal implant is manufactured via a traditional manufacturing technique and an additive manufacturing technique.

In some embodiments, the spinal implant system of the present disclosure comprises a spinal implant, surgical instrument and/or medical device having a hybrid configuration that combines a manufacturing method, such as, for example, one or more traditional manufacturing features and materials and a manufacturing method, such as, for example, one or more additive manufacturing features and materials. In some embodiments, additive manufacturing includes 3-D printing. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing and on-demand manufacturing.

In some embodiments, the spinal implant system of the present disclosure comprises a spinal implant, such as, for example, a bone screw manufactured by combining traditional manufacturing methods and additive manufacturing methods. In some embodiments, the bone screw is manufactured by applying additive manufacturing material in areas where the bone screw can benefit from materials and properties of additive manufacturing. In some embodiments, traditional materials are utilized where the benefits of these materials, such as physical properties and cost, are superior to those resulting from additive manufacturing features and materials.

In some embodiments, the bone screw is manufactured by combining traditional manufacturing methods and additive manufacturing such that a distal end of the bone screw is manufactured by additive manufacturing while a proximal end is manufactured by traditional methods and materials, such as, for example, subtractive manufacturing. In some embodiments, the proximal end is manufactured by wrought or from other materials that have enhanced physical properties relative to additive materials. In some embodiments, the distal end of the screw is subjected to higher loads and the physical properties of traditional materials offer benefits in performance and cost when compared to additive materials. In some embodiments, utilizing additive manufacturing to create the distal end of the bone screw can provide a bone in-growth surface along with complex internal and external features.

In some embodiments, the surgical system of the present disclosure comprises combining traditional manufacturing methods and materials with additive manufacturing to fabricate a spinal implant, such as, for example, a hybrid bone screw that facilitates bony fixation, ingrowth and purchase with tissue. In some embodiments, the hybrid bone screw provides improvement in stability of the bone screw when the distal end is engaged with tissue. In some embodiments, the bone screw is disposable with tissue in a cantilever configuration that supports a load on the hybrid bone screw in an even distribution. For example, a proximal portion of a bone screw fabricated from a traditional manufacturing method can include strength and stability features for supporting a load, for example, connection with a spinal rod. A distal portion of the bone screw fabricated from an additive manufacturing method can include fixation, ingrowth and porosity features, for example, to facilitate purchase with tissue. In some embodiments, applications of the present hybrid manufacturing technique employed for producing surgical instruments allows additive features to be added to a surgical instrument such that the surgical instrument includes selected features and/or features with complex internal geometry.

In some embodiments, the proximal end is manufactured by a traditional manufacturing method that employs a lathe, Swiss lathe, mill turning, whirling, grinding and/or roll forming. In some embodiments, the proximal end is disposed with a part, such as, for example, a build plate in connection with an additive forming technique. In some embodiments, the plate includes one or a plurality of openings configured for disposal of the proximal end. In some embodiments, the openings are threaded to facilitate connection of the proximal end with the plate. In some embodiments, the threaded surface is utilized to control thread orientation and timing of deposition and/or heating. In some embodiments, the openings are selectively shaped to facilitate connection with the proximal end. In some embodiments, the plate includes cavities, such as, for example, pockets that are selectively shaped to facilitate connection with the proximal end. In some embodiments, a distal face of the proximal end is engaged with one of the openings such that the distal face is disposed in a flush orientation with a surface of the plate. In some embodiments, the proximal end is disposed perpendicular to the plate. In some embodiments, the proximal end may be disposed in various orientations relative to the plate.

In some embodiments, the method of manufacturing the distal end includes a step of connecting the proximal end with the plate. In some embodiments, the method of manufacturing the distal end includes the step of providing a heat source to heat a powder deposited on the distal face of the proximal end. In some embodiments, the method of manufacturing the distal end includes the step of leveling the powder to a consistent thickness. In some embodiments, the method of manufacturing the distal end includes the step of melting the powder. In some embodiments, the method of manufacturing the distal end includes the step of translating the plate, such as, for example, in a downward direction to facilitate applying additional layers of the powder. In some embodiments, the method of manufacturing includes the step of disengaging the bone screw, such as, for example, by unscrewing the bone screw from the plate.

In some embodiments, the surgical system of the present disclosure comprises a threaded pedicle screw including a porous portion for enhancing bony fixation, ingrowth and purchase when implanted in bone. In some embodiments, the porous portion is manufactured on a distal surface of a proximal portion. In some embodiments, the porous portion is formed by 3-D printing. In some embodiments, the proximal portion of the bone screw is substantively manufactured and the distal portion is additively manufactured. In some embodiments, the distal portion may include needle-like protrusions and/or lattice structures, and/or protruding/depressed features, whether regular or irregular. In some embodiments, the materials utilized to manufacture the bone screw include stainless steel, titanium, cobalt-chromium, polymers, silicone, biologics and/or tissue. In some embodiments, the bone screw can be manufactured using wrought, forged, metal injection molded, roll formed, injection molded and/or machined materials, as described herein. In some embodiments, the distal portion is manufactured by additive manufacturing and connected with the proximal portion. In some embodiments, the distal portion is manufactured by additive manufacturing and mechanically attached with the proximal portion by, for example, welding, threading, adhesives and/or staking.

In some embodiments, the spinal implants, surgical instruments and/or medical devices of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the spinal implants, surgical instruments and/or medical devices of the present disclosure may be employed with other osteal and bone related applications, including those associated with diagnostics and therapeutics. In some embodiments, the spinal implants, surgical instruments and/or medical devices of the present disclosure may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions such as maxillofacial and extremities. The spinal implants, surgical instruments and/or medical devices of the present disclosure may also be alternatively employed with procedures for treating the lumbar, cervical, thoracic, sacral and pelvic regions of a spinal column. The spinal implants, surgical instruments and/or medical devices of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
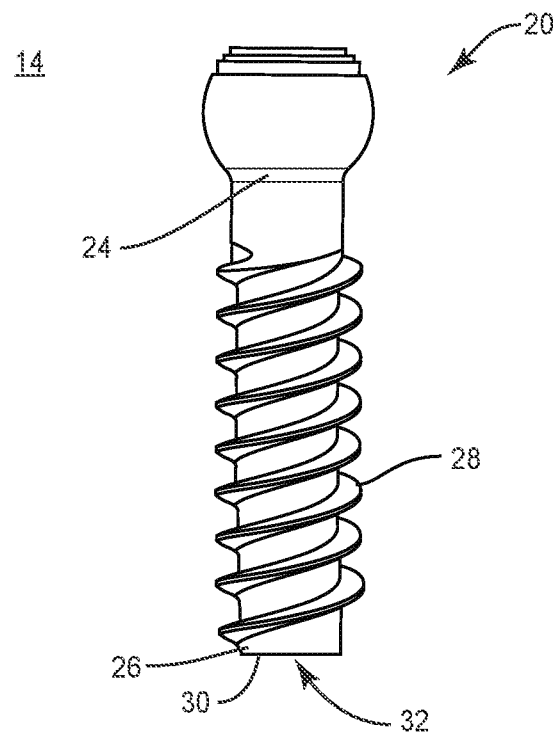
FIG. 2 is a side view of components of the system shown in FIG. 1.
Figure 3:
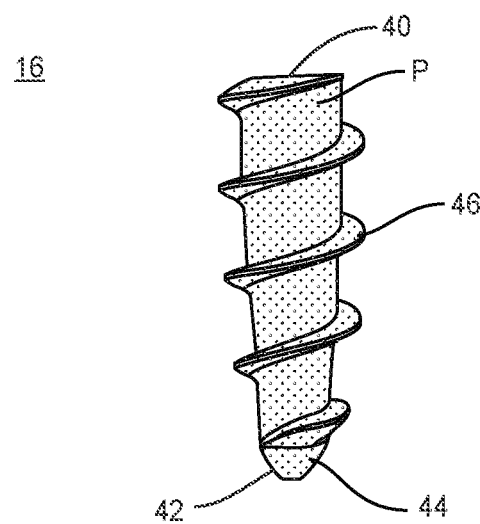
FIG. 3 is a side view of components of the system shown in FIG. 1.

The following discussion includes a description of a spinal implant, a method of manufacturing a spinal implant, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-3, there are illustrated components of a spinal implant system 10 including spinal implants, surgical instruments and medical devices.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant, such as, for example, a bone fastener 12 that defines a longitudinal axis X1. Bone fastener 12 includes an elongated screw shaft 18 having a proximal portion 14 fabricated by a first manufacturing method and a distal portion 16 fabricated by a second manufacturing method to enhance fixation and/or facilitate bone growth, as described herein. In some embodiments, the manufacturing method can include a traditional machining method, such as, for example, subtractive, deformative or transformative manufacturing methods. In some embodiments, the traditional manufacturing method may include cutting, grinding, rolling, forming, molding, casting, forging, extruding, whirling, grinding and/or cold working. In some embodiments, the traditional manufacturing method includes portion 14 being formed by a medical machining process. In some embodiments, medical machining processes can include use of computer numerical control (CNC) high speed milling machines, Swiss machining devices, CNC turning with living tooling, wire EDM 4th axis and/or Solid Works™ CAD, and Virtual Gibbs™ solid model rendering. In some embodiments, the manufacturing method for fabricating portion 14 includes a finishing process, such as, for example, laser marking, tumble blasting, bead blasting, micro blasting and/or powder blasting.

For example, portion 14 is formed by a manufacturing method, which includes feeding a straightened wire W into a machine that cuts wire W at a designated length to form a screw blank, as shown in FIG. 4, and die cuts a head of the screw blank into a selected configuration, as shown in FIG. 5. Portion 14 is manufactured to include a head 20 and a portion of screw shaft 18. Portion 14 extends between an end 24 and an end 26. End 24 includes head 20.

Portion 14 includes threads 28, which are fabricated by traditional machining methods, as described herein. Threads 28 extend along all or a portion of portion 14. Threads 28 are oriented with portion 14 and disposed for engagement with tissue. In some embodiments, threads 28 include a fine, closely-spaced configuration and/or shallow configuration to facilitate and/or enhance engagement with tissue. In some embodiments, threads 28 include a smaller pitch or more thread turns per axial distance to provide a stronger fixation with tissue and/or resist loosening from tissue. In some embodiments, threads 28 include a greater pitch and an increased lead between thread turns. In some embodiments, threads 28 are continuous along portion 14. In some embodiments, threads 28 are continuous along shaft 18 via a second manufacturing method, as described herein. In some embodiments, threads 28 may be intermittent, staggered, discontinuous and/or may include a single thread turn or a plurality of discrete threads. In some embodiments, other penetrating elements may be located on and/or manufactured with portion 14, such as, for example, a nail configuration, barbs, expanding elements, raised elements, ribs, and/or spikes to facilitate engagement of portion 14 with tissue.

End 26 includes a surface 30 that defines a distal face 32. In some embodiments, surface 30 may be disposed along a length of portion 14 or at a distalmost surface of portion 14. In some embodiments, distal face 32 extends perpendicular to axis X1, as shown in FIG. 6. In some embodiments, distal face 32 may be disposed in various orientations relative to axis X1, such as, for example, transverse and/or at angular orientations, such as acute or obtuse. In one embodiment, as shown in FIG. 7, distal face 32 is disposed at an acute angular orientation relative to axis X1.

Distal face 32 is configured for providing a fabrication platform for forming portion 16 thereon with an additive manufacturing method, as described herein. Distal face 32 has a substantially planar configuration for material deposition and/or heating during an additive manufacturing process for fabricating portion 16 onto distal face 32. In some embodiments, all or only a portion of distal face 32 may have alternate surface configurations, such as, for example, angled, irregular, uniform, non-uniform, offset, staggered, tapered, arcuate, undulating, mesh, porous, semi-porous, dimpled, pointed and/or textured. In some embodiments, distal face 32 may include a nail configuration, barbs, expanding elements, raised elements, ribs, and/or spikes to provide a fabrication platform for forming portion 16 thereon with an additive manufacturing method, as described herein. In some embodiments, all or only a portion of distal face 32 may have alternate cross section configurations, such as, for example, oval, oblong triangular, square, polygonal, irregular, uniform, non-uniform, offset, staggered, and/or tapered.

Portion 16 is fabricated with a second manufacturing method by disposing a material M onto distal face 32, as described herein. Portion 16 is configured for fabrication on distal face 32 such that portion 16 is fused with surface 30. Portion 16 is formed on distal face 32 by an additive manufacturing method. In some embodiments, portion 16 is fabricated by depositing material M onto distal face 32 one layer at a time, as described herein.

In some embodiments, additive manufacturing includes 3-D printing, as described herein. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing or on-demand manufacturing. In some embodiments, portion 16 is manufactured by additive manufacturing, as described herein, and mechanically attached with surface 30 by, for example, welding, threading, adhesives and/or staking.

Figure 8:
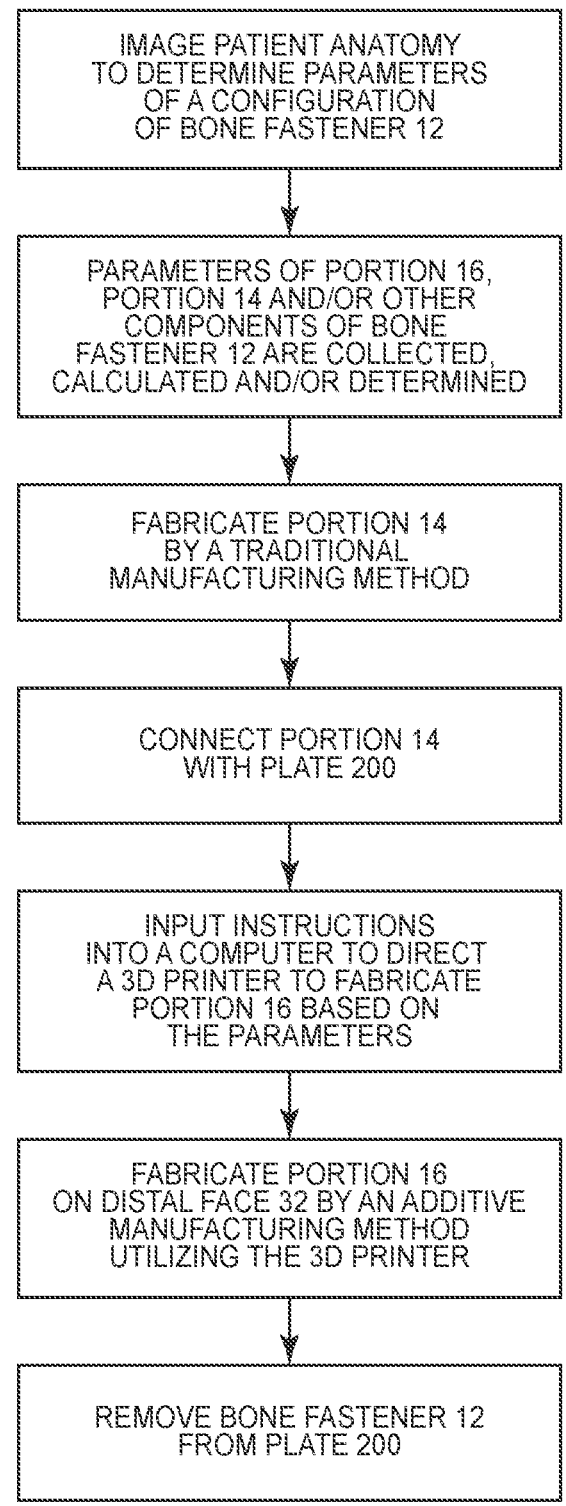
FIG. 8 is a flow diagram illustrating representative steps for producing components of one embodiment of a system in accordance with the principles of the present disclosure.

In one embodiment, as shown in FIG. 8, one or more manufacturing methods for fabricating distal portion 16, proximal portion 14 and/or other components of bone fastener 12 include imaging patient anatomy with imaging techniques, such as, for example, x-ray, fluoroscopy, computed tomography (CT), magnetic resonance imaging (MRI), surgical navigation, and/or acquirable 2-D or 3-D images of patient anatomy. Selected configuration parameters of distal portion 16, proximal portion 14 and/or other components of bone fastener 12 are collected, calculated and/or determined. Such configuration parameters can include one or more of patient anatomy imaging, surgical treatment, historical patient data, statistical data, treatment algorithms, implant material, implant dimensions, porosity and/or manufacturing method. In some embodiments, the configuration parameters can include implant material and porosity of distal portion 16 determined based on patient anatomy and the surgical treatment. In some embodiments, the implant material includes a selected porosity P of distal portion 16, as described herein. In some embodiments, the selected configuration parameters of distal portion 16, proximal portion 14 and/or other components of bone fastener 12 are patient specific. In some embodiments, the selected configuration parameters of distal portion 16, proximal portion 14 and/or other components of bone fastener 12 are based on generic or standard configurations and/or sizes and not patient specific. In some embodiments, the selected configuration parameters of distal portion 16, proximal portion 14 and/or other components of bone fastener 12 are based on one or more configurations and/or sizes of components of a kit of spinal implant system 10 and not patient specific.

For example, based on one or more selected configuration parameters, as described herein, a digital rendering and/or data of a selected distal portion 16, proximal portion 14 and/or other components of bone fastener 12, which can include a 2-D or a 3-D digital model and/or image, is collected, calculated and/or determined, and generated for display from a graphical user interface, as described herein, and/or storage on a database attached to a computer and a processor (not shown), as described herein. In some embodiments, the computer provides the ability to display, via a monitor, as well as save, digitally manipulate, or print a hard copy of the digital rendering and/or data. In some embodiments, a selected distal portion 16, proximal portion 14 and/or other components of bone fastener 12 can be designed virtually in the computer with a CAD/CAM program, which is on a computer display. In some embodiments, the processor may execute codes stored in a computer-readable memory medium to execute one or more instructions of the computer, for example, to transmit instructions to an additive manufacturing device, such as, for example, a 3-D printer. In some embodiments, the database and/or computer-readable medium may include RAM, ROM, EPROM, magnetic, optical, digital, electromagnetic, flash drive and/or semiconductor technology. In some embodiments, the processor can instruct motors (not shown) that control movement and rotation of spinal implant system 10 components, for example, a build plate 200, distal face 32 and/or laser emitting devices, as described herein.

In some embodiments, the components of spinal implant system 10 can include one or more computer systems. In some embodiments, the components of spinal implant system 10 can include computers and/or servers of a network having a plurality of computers linked to each other over the network, Wi-Fi, Internet, comprise computers connected via a cloud network or in a data drop box. In some embodiments, the graphical user interface may include one or more display devices, for example, CRT, LCD, PDAs, WebTV terminals, set-top boxes, cellular phones, screen phones, smart phones, iPhone, iPad, tablet, wired or wireless communication devices.

Figure 9:
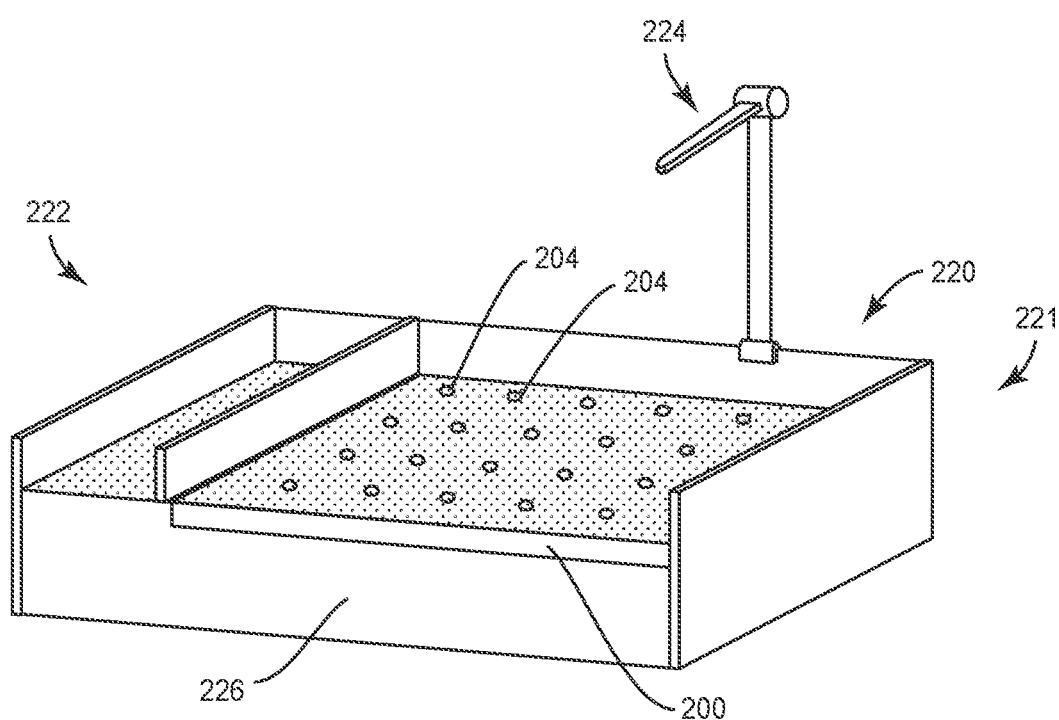
FIG. 9 is a perspective view of components of one embodiment of a system in accordance with the principles of the present disclosure.
Figure 10:
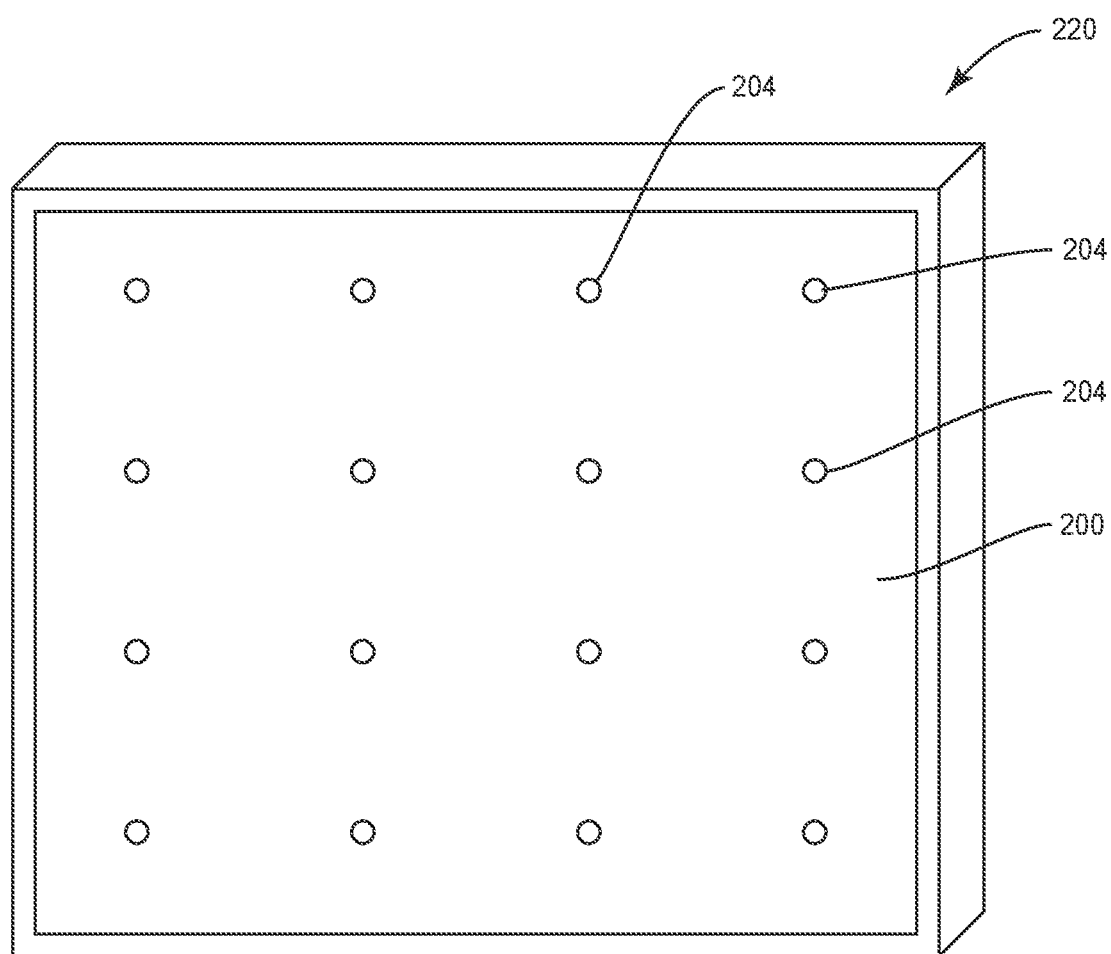
FIG. 10 is a perspective view of components of one embodiment of a system in accordance with the principles of the present disclosure.

Portion 14 is fabricated with threads 28 by a first manufacturing method, as described herein. Portion 14 is connected with a part, such as, for example, a build plate 200 in connection with an additive forming process and a second manufacturing method for fabricating distal portion 16. Build plate 200 is selectively configured for fabricating a selectively configured distal portion 16, as described herein, and disposed with a working chamber 220 of a powder bed additive manufacturing apparatus 222, as shown in FIGS. 9 and 10. An enclosure 221 of apparatus 222 defines working chamber 220.

Apparatus 222 includes a heating device, such as, for example, a laser device 224 disposed with working chamber 220 that fuses material M, which includes a powder, as described herein, in a slice by slice, layer by layer formation of portion 16 onto distal face 32. In some embodiments, laser device 224 includes an interactive laser and optics system that produces a laser beam scanned over a layer of material M powder disposed on build plate 200 to selectively heat the powder according to instructions received from the computer and processor based on the digital rendering and/or data of the selected configuration of portion 16. Laser device 224 heats a thin layer of material M powder in accordance with slice data based on the digital rendering and/or data to fabricate portion 16, layer by layer, via an additive manufacturing technique. See, for example, the additive and three dimensional manufacturing systems and methods described in U.S. Pat. No. 5,204,055 and US Patent Application Publication No. 2014/0252685, the contents of each of these references being hereby incorporated by reference herein in their respective entireties.

Figure 11:
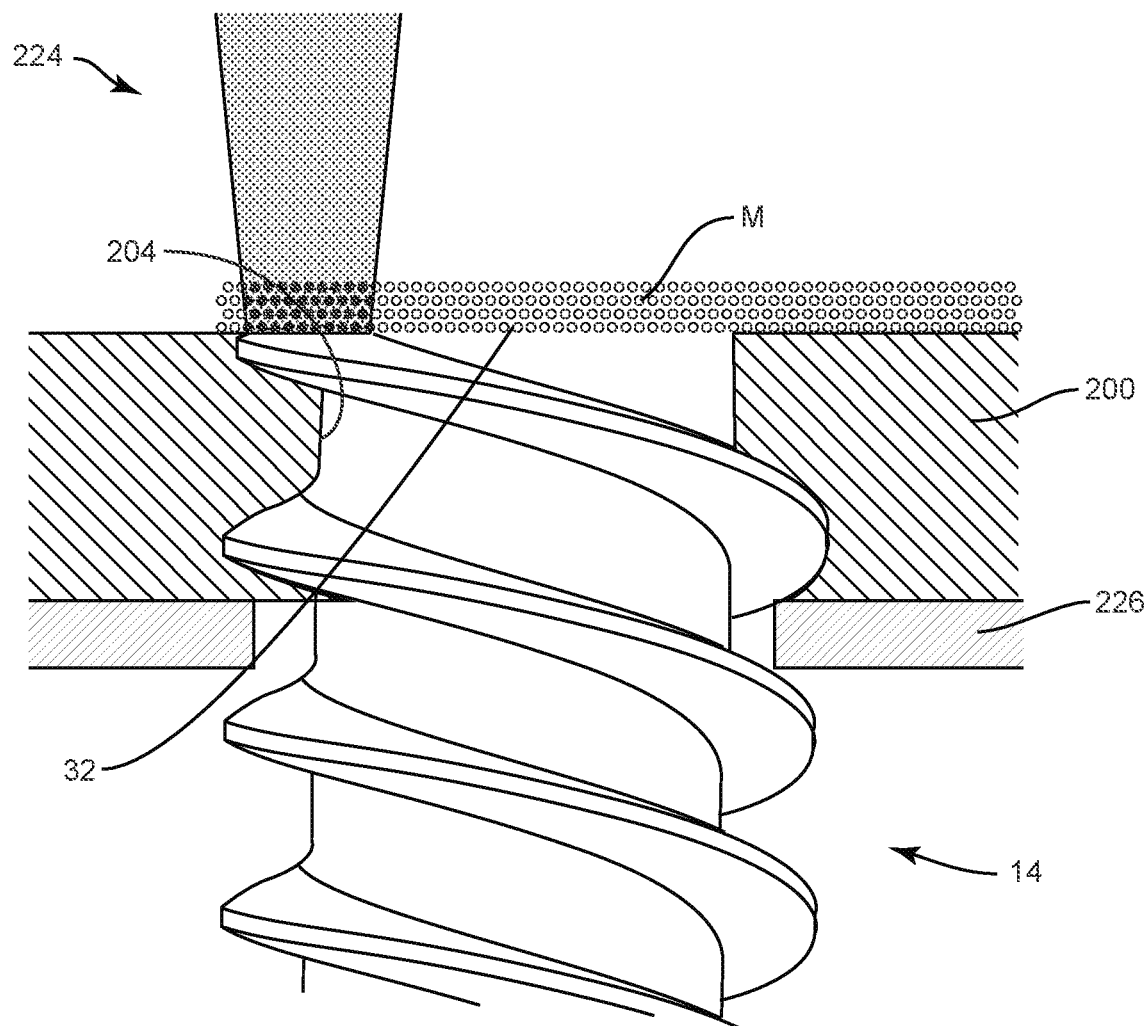
FIG. 11 is a side view, in part cross section, of components of one embodiment of a system in accordance with the principles of the present disclosure.

In some embodiments, apparatus 222 includes a radiation source that melts and solidifies material M disposed with distal face 32 into a desired three-dimensional shape based on the selected configuration parameters, as described herein. In some embodiments, the radiation source includes laser device 224, which comprises a carbon dioxide laser. In some embodiments, laser device 224 may include a beam of any wavelength of visible light or UV light. In some embodiments, apparatus 222 emits alternative forms of radiation, such as, for example, microwave, ultrasound or radio frequency radiation. In some embodiments, laser device 224 is configured to be focused on a portion of distal face 32 to sinter material M deposited thereon, as shown in FIG. 11. In some embodiments, laser device 224 emits a beam having a diameter between about 0.01 mm and about 0.8 mm. In some embodiments, the diameter of the beam may be between about 0.1 mm and about 0.4 mm. In some embodiments, the diameter of the beam is adjustable to customize the intensity of the sintering.

Figure 12:
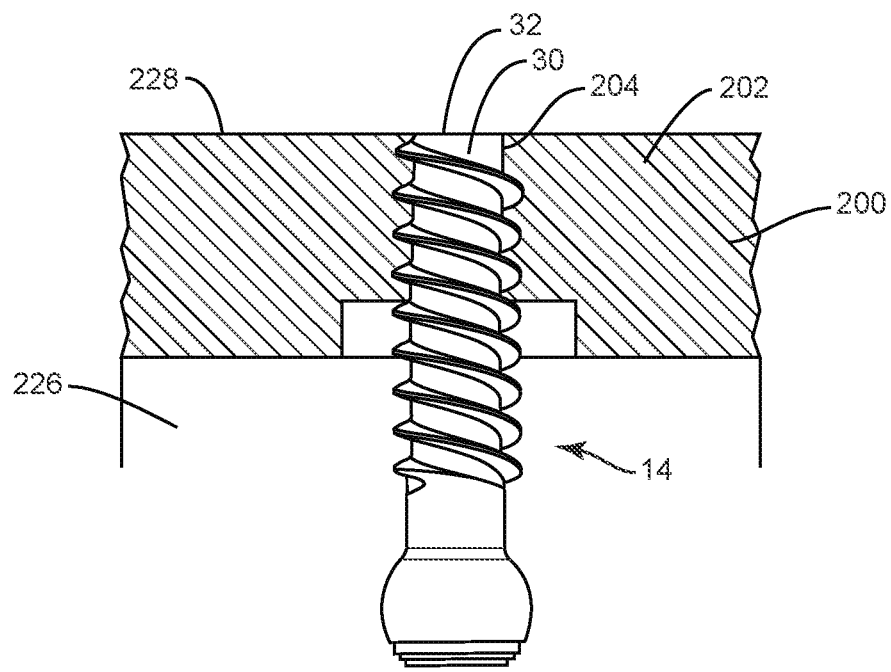
FIG. 12 is a side view, in part cross section, of components of one embodiment of a system in accordance with the principles of the present disclosure.
Figure 13:
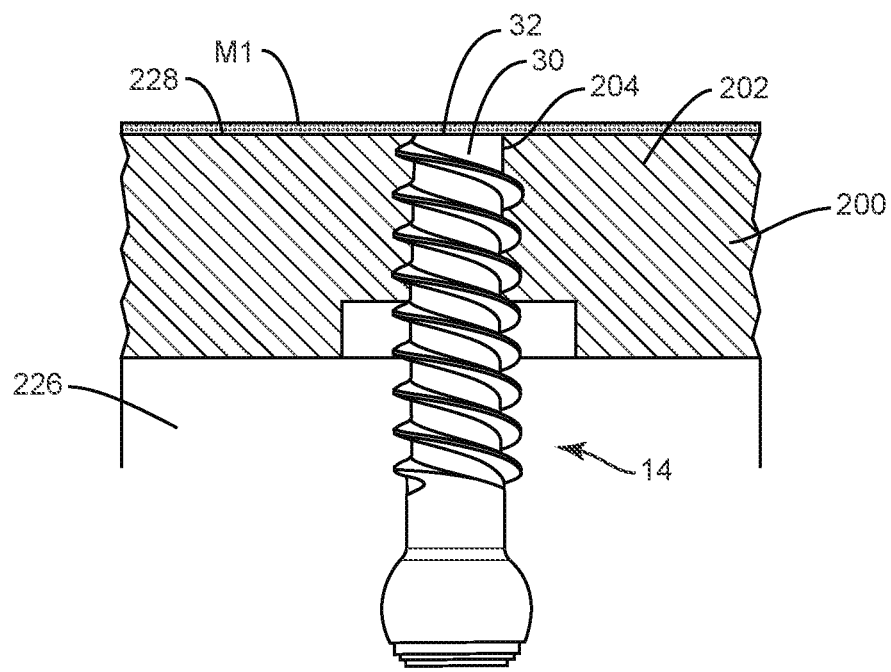
FIG. 13 is a side view, in part cross section, of components of one embodiment of a system in accordance with the principles of the present disclosure.

Build plate 200 includes a surface 202 that defines one or a plurality of openings 204. Each opening 204 is configured for disposal of proximal portion 14 to orient distal face 32 as a fabrication platform for forming portion 16 thereon with an additive manufacturing method, as described herein. The portions of surface 202 that define openings 204 are threaded with surface 30 to facilitate connection with portion 14. Portion 14 is threaded with openings 204, as shown in FIG. 12. Distal face 32 is disposed with opening 204 in a flush orientation with surface 202, as shown in FIG. 13, to orient distal face 32 for selective laser melting with a powder bed process by apparatus 222.

In some embodiments, openings 204 are oriented with plate 200 to control thread orientation and timing of deposition and/or heating of material M with distal face 32 to fabricate portion 16 in accordance with selected configuration parameters, as described herein. Surface 30 is threaded with surface 202 and distal face 32 is disposed with opening 204 in a perpendicular orientation relative to surface 202 and axis X1, as shown in FIG. 6. In some embodiments, distal face 32 may be disposed with opening 204 in various orientations relative to surface 202, such as, for example, transverse and/or at angular orientations, such as acute or obtuse. In one embodiment, as shown in FIG. 7, surface 30 is threaded with surface 202 and distal face 32 is disposed with opening 204 at an acute angular orientation relative to axis X1. In some embodiments, portion 14 may be disposed with opening 204 in alternate connection configurations, such as, for example, friction fit, pressure fit, locking protrusion/recess, locking keyway and/or adhesive.

In some embodiments, surface 202 includes pockets (not shown) disposed adjacent openings 204 that are selectively shaped to form selective configurations of portion 16, as described herein. In some embodiment plate 200 may be substantially non-conductive. In some embodiments, plate 200 may be ceramic, glass or non-metallic. In some embodiments, plate 200 may be formed of an electrical insulating material that is operable to prevent an external heat control mechanism from heating plate 200 to a sintering temperature of material M that is utilized to form the layers.

Build plate 200 is mounted with a platform 226 of apparatus 222 such that build plate 200 can be moved relative to enclosure 221 in one or more directions to generate distal portion 16 onto distal face 32, layer by layer, based on the digital rendering and/or data. In some embodiments, build plate 200 can be translated vertically, horizontally or diagonally, rotated, pivoted, raised and/or lowered to generate distal portion 16. In some embodiments, build plate 200 can be moved relative to enclosure 221 slidably, continuously, incrementally, intermittently, automatically, manually, selectively and/or via computer/processor control. In some embodiments, apparatus 222 comprises an additive manufacturing device that employs selective laser melting with a powder bed process to create 3D objects. See, for example, the Lasertec 30 SLM additive manufacturing machine manufactured by DMG MORI Co. Ltd. located at 2-35-16 Meieki, Nakamura-ku, Nagoya City 450-0002, Japan.

In some embodiments, apparatus 222 is connected with one or more computer systems, processors and databases, as described herein, to receive commands and instructions for creating distal portion 16 onto distal face 32 by selective laser melting with a powder bed process by apparatus 222. For example, the commands and instructions are based on the one or more selected configuration parameters of a selected distal portion 16 generated for display from a graphical user interface and/or stored on a database, as described herein. In some embodiments, apparatus 222 and/or the one or more computer systems can include a keyboard to input commands and instructions. In some embodiments, the processor receives the instructions and directs apparatus 222 to fabricate portion 16 based on the received instructions.

Material M powder is introduced in working chamber 220. Apparatus 222 includes a coating arm (not shown) that translates within working chamber 220 to deposit layers of material M powder along a planar surface 228 of plate 200. In some embodiments, the coating arm includes a blade that executes a displacement motion to sweep and/or deposit material M powder across distal face 32 and surface 228. In some embodiments, material M is introduced over the entire cross section of working chamber 220. Material M is leveled by the blade to a uniform and/or consistent thickness according to the selected configuration parameters, as described herein. In some embodiments, a powder bed is formed around portion 16 by excess powder accumulated during manufacture of each layer of portion 16. In some embodiments, the powder bed is configured as a support material during fabrication of portion 16 as the part being constructed is surrounded by un-sintered powder at all times. In some embodiments, material M may include, such as, for example, stainless steel, titanium, cobalt-chromium, polymers, silicone, biologics and/or tissue. In some embodiments, a layer volume of material M powder may be, such as, for example, 300×300×300 mm. In some embodiments, a cartridge-type supply/collection system for material M is provided to facilitate powder delivery and recycling.

Figure 14:
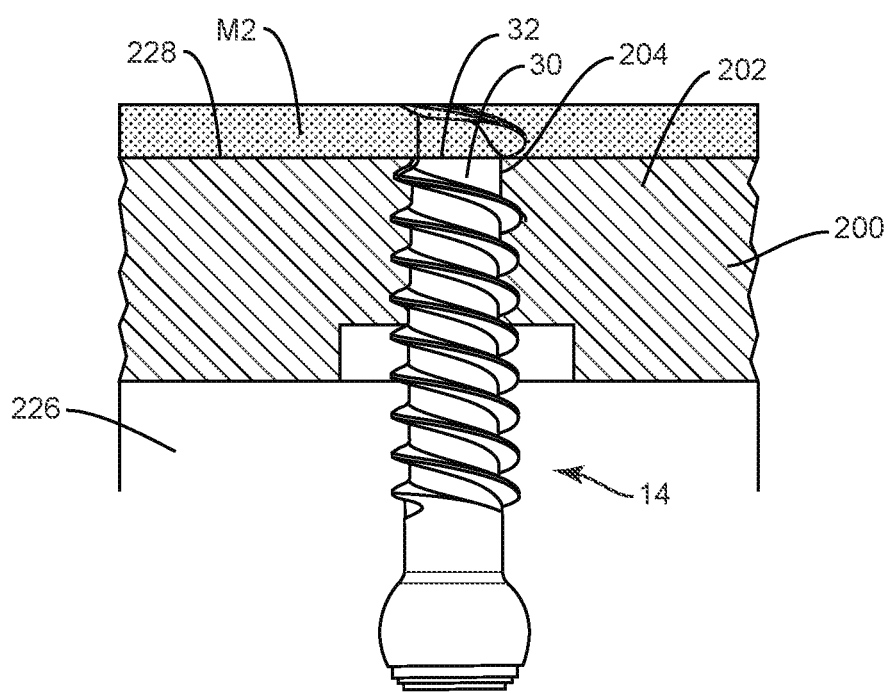
FIG. 14 is a side view, in part cross section, of components of one embodiment of a system in accordance with the principles of the present disclosure.

Laser device 224 focuses a laser beam to a layer M1 of material M powder disposed with surface 228, as shown in FIG. 13. Laser device 224 heats, melts and/or softens layer M1 to selectively heat material M powder according to instructions received from the computer and processor based on the digital rendering and/or data of the selected configuration to produce a layer of portion 16, as shown in FIG. 14. Laser device 224 articulates relative to plate 200 such that the supplied beam is focused on the selected portions of material M deposited on distal face 32. The beam is focused onto portions of material M on distal face 32 to melt or sinter material M into a desired shape based on the selected configuration parameters. Platform 226 moves plate 200 relative to enclosure 221, as described herein, for example, vertically downward to translate portion 16 during fabrication of the successive layers of portion 16 according to instructions received from the computer and processor.

After one layer of portion 16 is melted, plate 200 and the fabricated layer of portion 16 is translated vertically downward to align the fabricated layer such that the blade moves across surface 228 to sweep and/or deposit another layer M2 of material M powder across the prior fabricated layer on distal face 32 and plate 200 for melting, as shown in FIG. 14. Layer M2 is leveled by the blade to a thickness according to the selected configuration parameters, as described herein. Laser device 224 heats, melts and/or softens layer M2 to selectively heat material M powder to produce a successive layer of portion 16 according to instructions received from the computer and processor.

Figure 15:
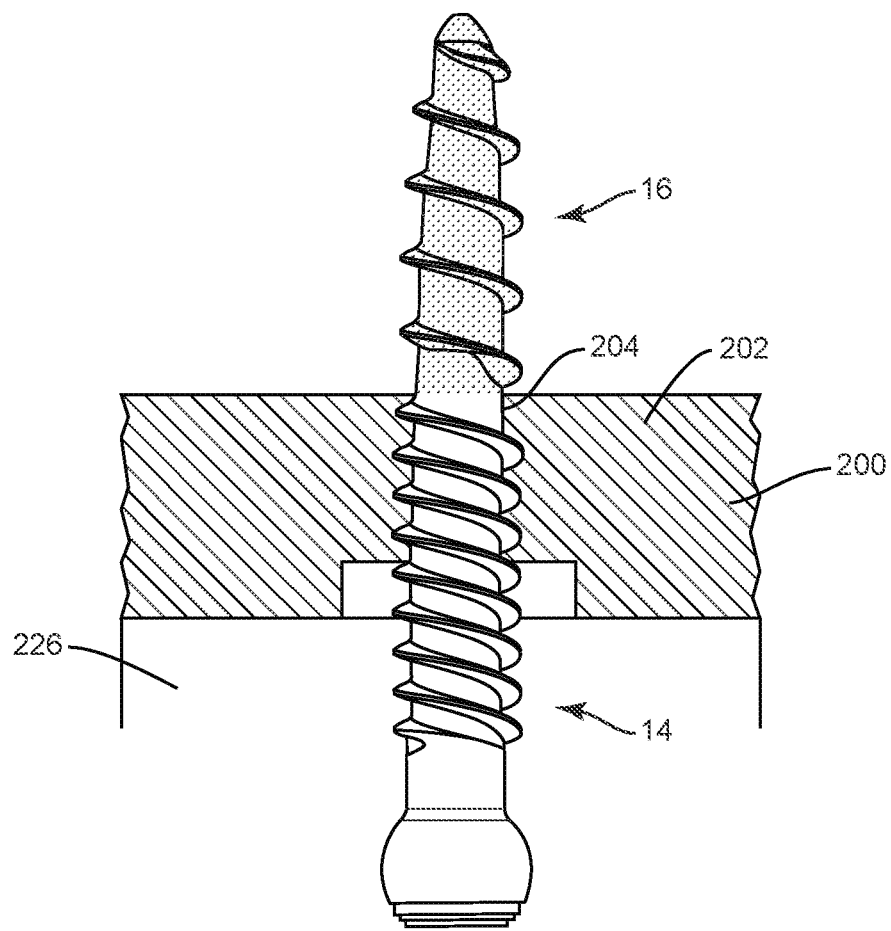
FIG. 15 is a side view, in part cross section, of components of one embodiment of a system in accordance with the principles of the present disclosure.

Portion 16 is built up layer by layer and the melting process is repeated slice by slice, layer by layer, until the final layer of material M is melted and portion 16 is complete, as shown in FIG. 15. Portion 16 is formed on distal face 32 to extend between an end 40 and end 42 according to instructions received from the computer and processor, and end 40 is fused with surface 30. End 42 includes a distal tip 44. In some embodiments, material M is subjected to direct metal laser sintering (DMLS®), selective laser sintering (SLS), fused deposition modeling (FDM), or fused filament fabrication (FFF), or stereolithography (SLA).

Portion 16 is fabricated according to instructions received from the computer and processor based on the digital rendering and/or data of the selected configuration, via the additive manufacturing process described herein to include a thread 46 that extends between end 40 and distal tip 44. Thread 46 is formed layer by layer by fabrication of portion 16, as described herein. Thread 46 is fabricated to extend along all or a portion of portion 16. In some embodiments, thread 46 is fabricated to include a fine, closely-spaced and/or shallow configuration to facilitate and/or enhance engagement with tissue. In some embodiments, thread 46 is fabricated to include a greater pitch and an increased lead between thread turns than thread 28, as shown in FIG. 1. In some embodiments, thread 46 is fabricated to include a smaller pitch or more thread turns per axial distance than thread 28 to provide a stronger fixation with tissue and/or resist loosening from tissue. In some embodiments, thread 46 is fabricated to be continuous along portion 16. In some embodiments, thread 46 is fabricated to be continuous along portion 16. In some embodiments, thread 46 is fabricated to be intermittent, staggered, discontinuous and/or may include a single thread turn or a plurality of discrete threads. In some embodiments, portion 16 is fabricated to include penetrating elements, such as, for example, a nail configuration, barbs, expanding elements, raised elements, ribs, and/or spikes. In some embodiments, thread 46 is fabricated to be self-tapping or intermittent at distal tip 44. In some embodiments, distal tip 44 may be rounded. In some embodiments, distal tip 44 may be self-drilling.

Bone fastener 12 is disengaged from plate 200 upon fabrication of portion 16 via an additive manufacturing method, as described herein. For example, portion 14 is removed from opening 204 of plate 200 such that surface 30 is unthreaded from surface 202. In some embodiments, portion 16 is subjected to a finishing process, such as, for example, laser marking, tumble blasting, bead blasting, micro blasting and/or powder blasting. In some embodiments, the additive manufacturing method may include a 3-D printing head. In some embodiments, the additive manufacturing method may include a temperature control unit such as, for example, a heating or cooling unit to control a temperature of distal face 32. In some embodiments, the computer and processor provide instructions for coordination of simultaneous and/or ordered movement of plate 200, distal face 32, laser device 224, components of apparatus 222 and/or introduction and layering of material M powder.

In some embodiments, portion 16 is fabricated in a configuration having a porosity P via the additive manufacturing method, as described herein. In some embodiments, portion 16 is fabricated having a porosity P with a porogen that is spheroidal, cuboidal, rectangular, elongated, tubular, fibrous, disc-shaped, platelet-shaped, polygonal or a mixture thereof. In some embodiments, a porosity of portion 16 is based on a plurality of macropores, micropores, nanopores structures and/or a combination thereof.

In some embodiments, the porogen is configured to diffuse, dissolve, and/or degrade after implantation into portion 16 leaving a pore. The porogen may be a gas (e.g., carbon dioxide, nitrogen, argon or air), liquid (e.g., water, blood lymph, plasma, serum or marrow), or solid (e.g., crystalline salt, sugar). The porogen may be a water-soluble chemical compound such as a carbohydrate (e.g., polydextrose, dextran), salt, polymer (e.g., polyvinyl pyrrolidone), protein (e.g., gelatin), pharmaceutical agent (e.g., antibiotics), or a small molecule. In other aspects, the porous implant includes as a porogen polysaccharides comprising cellulose, starch, amylose, dextran, poly(dextrose), glycogen, poly(vinylpyrrolidone), pullulan, poly(glycolide), poly(lactide), and/or poly(lactide-co-glycolide). In other aspects, the useful porogens include without limitations hydroxyapatite or polyethylene oxide, polylactic acid, polycaprolactone. Peptides, proteins of fifty amino acids or less or a parathyroid hormone are also useful porogens.

In some embodiments, the porous configuration of portion 16 can exhibit high degrees of porosity over a wide range of effective pore sizes. In some embodiments, the porous configuration of portion 16 may have, at once, macroporosity, mesoporosity, microporosity and nanoporosity. Macroporosity is characterized by pore diameters greater than about 100 microns. Mesoporosity is characterized by pore diameters between about 100 microns about 10 microns; and microporosity occurs when pores have diameters below about 10 microns. Microporous implants have pores of diameters below 9 microns, 8 microns, 7 microns, 6 microns, 5 microns, 4 microns, 3 microns, 2 microns, and 1 micron. Nanoporosity of nanopores is characterized by pore diameters of about 1 nm and below.

In some embodiments, portion 16 is fabricated with a material having a porosity P that is created by an additive manufacturing method, as described herein, of a polymer material, for example, a polymer, onto a bed of particles which are not soluble in the polymer and which can be subsequently leached by a non-solvent for the polymer. In this case, the polymer which forms portion 16 is printed onto a bed of particles such as salt, sugar, or polyethylene oxide. After the additive manufacturing method is complete, portion 16 is removed from the powder bed and placed in a non-solvent for the implant material which will dissolve the particles. For example, polylactic acid in chloroform could be 3-D printed onto a bed of sugar particles, and the sugar can subsequently be leached with water.

In some embodiments, portion 16 is fabricated with a material having a porosity P that is created by an additive manufacturing method, as described herein, by printing a solution containing an implant material onto a heated bed of polymer. An example is 3-D printing polylactic acid in chloroform onto a bed of PLA particles heated to 100° C. The boiling point of chloroform is 60° C., and it will thus boil on hitting the particle bed, causing a foam to form. This method of creating porosity is similar to 3-D printing a solution containing the implant material onto a bed containing a foaming agent, which is another way of achieving porosity.

In some embodiments, bone fastener 12 includes an implant receiver (not shown) connectable with head 20. In some embodiments, bone fastener 12 can include various configurations, such as, for example, a posted screw, a pedicle screw, a bolt, a bone screw for a lateral plate, an interbody screw, a uni-axial screw, a fixed angle screw, a multi-axial screw, a side loading screw, a sagittal adjusting screw, a transverse sagittal adjusting screw, an awl tip, a dual rod multi-axial screw, midline lumbar fusion screw and/or a sacral bone screw. In some embodiments, the implant receiver can be attached by manual engagement and/or non-instrumented assembly, which may include a practitioner, surgeon and/or medical staff grasping the implant receiver and shaft 18 and forcibly snap or pop fitting the components together. In some embodiments, spinal implant system 10 comprises a kit including a plurality of bone fasteners 12 of varying configuration, as described herein. In some embodiments, bone fastener 12 is selected from the kit and employed with a treatment at the surgical site.

Figure 16:
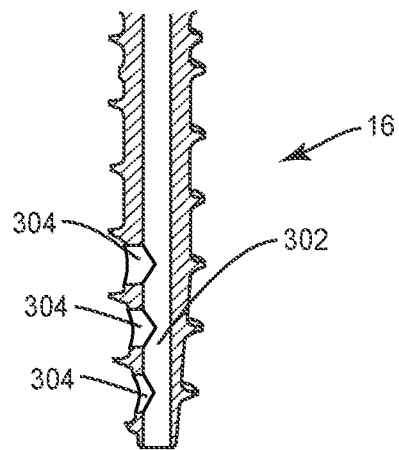
FIG. 16 is a side, cross section view of components of one embodiment of a system in accordance with the principles of the present disclosure.
Figure 17:
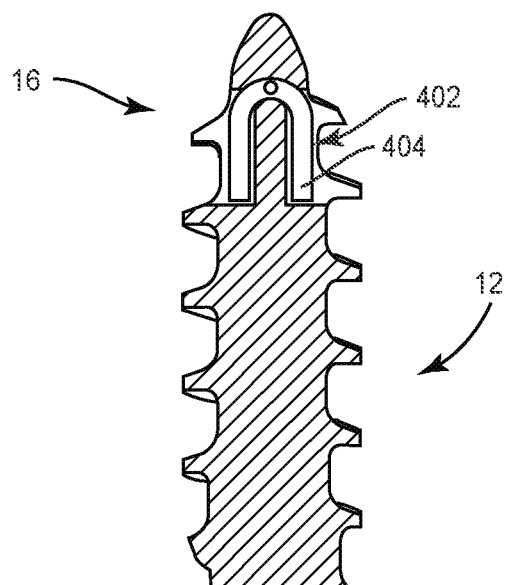
FIG. 17 is a side, cross section view of components of one embodiment of a system in accordance with the principles of the present disclosure.
Figure 18:
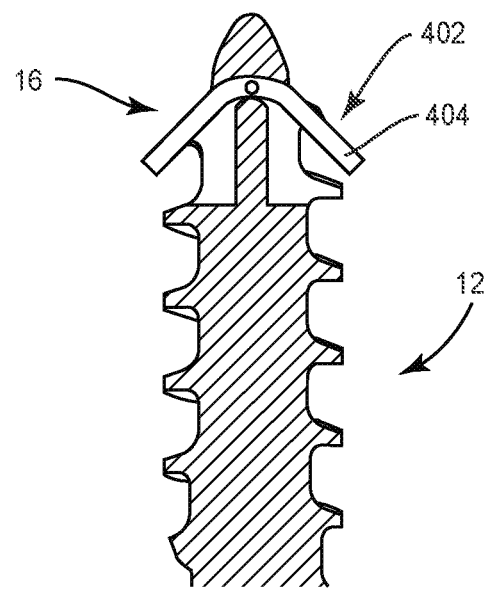
FIG. 18 is a side, cross section view of components of one embodiment of a system in accordance with the principles of the present disclosure.

In one embodiment, as shown in FIG. 16, portion 16 is fabricated with an additive manufacturing method, as described herein, to define a passageway 302 such that portion 16 includes a cannulated configuration and a plurality of lateral fenestrations 304 in communication with passageway 302. In some embodiments, portion 14 may be fabricated with a traditional manufacturing method, as described herein, to similarly define a portion of passageway 302 and fenestrations in communication with passageway 302. In one embodiment, as shown in FIGS. 17 and 18, portion 16 is fabricated with an additive manufacturing method, as described herein, to include a mechanical lock, such as, for example, an expanding barb 402 having rotatable arms 404 that pivot outwardly to facilitate engagement with tissue.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An additive manufacturing apparatus comprising:
an enclosure including opposite front and back walls and opposite first and second side walls each extending from the front wall to the back wall, inner surfaces of the walls defining a chamber;
a build plate mounted with the enclosure, the build plate comprising opposite proximal and distal surfaces, the build plate defining a plurality of spaced apart openings each extending through the proximal and distal surfaces such that the openings are each in communication with the chamber, the openings each being configured for disposal of a screw shaft; and
a heating device coupled to the back wall and configured to heat a material applied to the screw shafts to fuse the material with the screw shafts,
wherein the build plate mounted with a platform of the enclosure defined by the front wall such that the build plate is movable relative to the enclosure in one or more directions, and
wherein the openings each define a female thread, the openings each including a proximal portion that extends through the proximal surface and a distal portion that extends through the distal surface, the proximal portions having a diameter that is greater than a diameter of the distal portions, the diameters of the proximal and distal portions each being greater than a major diameter of the female threads.

2. An additive manufacturing apparatus as recited in claim 1, further comprising a coating arm, the coating arm including a blade that is configured to execute a displacement motion to sweep the material across the proximal surface.

3. An additive manufacturing apparatus as recited in claim 1, wherein the heating device comprises a laser device, the laser device including an interactive laser and optics system that produces a laser beam.

4. An additive manufacturing apparatus as recited in claim 1, wherein the build plate is non-conductive.

5. An additive manufacturing apparatus comprising:
an enclosure defining a chamber; and
a build plate mounted with the enclosure, the build plate comprising opposite proximal and distal surfaces, the build plate defining a plurality of spaced apart openings each extending through the proximal and distal surfaces such that the openings are each in communication with the chamber, the openings each being configured for disposal of a screw shaft, the openings each defining a female thread, the openings each including a proximal portion and a distal portion, the proximal portions having a first diameter and the distal portions having a second diameter, the first and second diameters each being greater than a major diameter of the female threads.

6. An additive manufacturing apparatus as recited in claim 5, wherein the first diameters are greater than the second diameters.

7. An additive manufacturing apparatus as recited in claim 5, wherein the proximal portions extend through the proximal surface and the distal portions extend through the distal surface.

8. An additive manufacturing apparatus as recited in claim 5, wherein the build plate is mounted with the enclosure such that the build plate is movable relative to the enclosure in at least one direction.

9. An additive manufacturing apparatus as recited in claim 8, wherein the at least one direction includes a plurality of directions.

10. An additive manufacturing apparatus as recited in claim 5, wherein the enclosure includes opposite front and back walls and opposite first and second side walls each extending from the front wall to the back wall, inner surfaces of the walls defining the chamber.

11. An additive manufacturing apparatus as recited in claim 5, further comprising a heating device coupled to the enclosure and configured to heat a material applied to the screw shafts to fuse the material with the screw shafts.

12. An additive manufacturing apparatus as recited in claim 11, wherein the heating device comprises a laser device, the laser device including an interactive laser and optics system that produces a laser beam.

13. An additive manufacturing apparatus as recited in claim 11, further comprising a coating arm, the coating arm including a blade that is configured to execute a displacement motion to sweep the material across the proximal surface.

14. An additive manufacturing apparatus as recited in claim 5, wherein the build plate is non-conductive.

15. An additive manufacturing apparatus comprising:
an enclosure defining a chamber; and
a non-conductive build plate mounted with the enclosure, the build plate defining a plurality of spaced apart openings extending therethrough such that the openings are each in communication with the chamber, the openings each defining a female thread, the openings each including a proximal portion and a distal portion, the proximal portions having a first diameter and the distal portions having a second diameter, the first and second diameters each being greater than a major diameter of the female threads.

16. An additive manufacturing apparatus as recited in claim 15, wherein the first diameters are greater than the second diameters.

17. An additive manufacturing apparatus as recited in claim 15, wherein the build plate is mounted with the enclosure such that the build plate is movable relative to the enclosure in at least one direction.

18. An additive manufacturing apparatus as recited in claim 17, wherein the at least one direction includes a plurality of directions.

19. An additive manufacturing apparatus as recited in claim 15, further comprising a heating device coupled to the enclosure and configured to heat a material that can be applied to screw shafts positioned in the openings to fuse the material with the screw shafts.

20. An additive manufacturing apparatus as recited in claim 19, wherein the heating device comprises a laser device, the laser device including an interactive laser and optics system that produces a laser beam.

* * * * *